(12) United States Patent
Woo et al.

(10) Patent No.: US 8,454,991 B2
(45) Date of Patent: Jun. 4, 2013

(54) METHOD AND DEVICE FOR PHOTODYNAMIC THERAPY

(75) Inventors: Thomas Woo, Edmonton (CA); Gerald George Miller, Montville (AU); Ragupathy Madiyalakan, Edmonton (CA)

(73) Assignee: Quest Pharmatech Inc.

( * ) Notice: Subject to any disclaimer, the term of this patent is extended or adjusted under 35 U.S.C. 154(b) by 1063 days.

(21) Appl. No.: 12/302,812

(22) PCT Filed: Jul. 17, 2007

(86) PCT No.: PCT/CA2007/001290
§ 371 (c)(1),
(2), (4) Date: Nov. 28, 2008

(87) PCT Pub. No.: WO2008/011707
PCT Pub. Date: Jan. 31, 2008

(65) Prior Publication Data
US 2009/0204057 A1    Aug. 13, 2009

Related U.S. Application Data

(60) Provisional application No. 60/820,171, filed on Jul. 24, 2006.

(51) Int. Cl.
*A61F 13/00* (2006.01)
*A61K 9/70* (2006.01)
(52) U.S. Cl.
USPC ........................................................ 424/449
(58) Field of Classification Search
USPC ........................................................ 424/449
See application file for complete search history.

(56) References Cited

U.S. PATENT DOCUMENTS 5,474,528 A * 12/1995 Meserol ............................ 604/20
5,705,103 A *  1/1998 Chopdekar et al. ............ 252/700

(Continued)

FOREIGN PATENT DOCUMENTS

| CN | 1600771 | 3/2005 |
| CN | 1600780 | 3/2005 |

(Continued)

OTHER PUBLICATIONS

Babilas et al. "In vitro and in vivo comparison of two different light sources for topical photodynamic therapy" The British Journal of Dermatolofgy, Apr. 2006, 154(4), 712 718.

(Continued)

*Primary Examiner* — Benjamin Packard
(74) *Attorney, Agent, or Firm* — Sheridan Ross P.C.

(57) ABSTRACT

The present invention relates to a photodynamic therapy method and uses thereof for treating an individual in need thereof, comprising administering a photosensitizer to an individual and activating the photosensitizer with a chemiluminescent light source, and/or a light-emitting diode light source, wherein the light source is in dermal contact with the individual. The present invention also relates to a device for photodynamic therapy comprising a permeable reservoir, for containing a photosensitizer formulation for skin application, the device is adapted to deliver the photosensitizer to the individual. The present invention also relates to a device for photodynamic therapy, comprising a permeable reservoir for containing a photosensitizer formulation for skin application and a light source. The light source is a chemiluminescent light source or a light-emitting diode light source and the device is adapted to deliver the photosensitizer to the individual and to irradiate a part of an individual to activate the photosensitizer.

11 Claims, 5 Drawing Sheets

U.S. PATENT DOCUMENTS

| | | | |
|---|---|---|---|
| 5,952,311 | A | 9/1999 | Kraus et al. |
| 6,498,148 | B1 | 12/2002 | Raz |
| 6,593,370 | B2 * | 7/2003 | Tamura et al. ............... 514/627 |
| 2002/0022032 | A1 | 2/2002 | Curry et al. |
| 2002/0041864 | A1 | 4/2002 | Fanslow et al. |
| 2002/0183301 | A1 * | 12/2002 | Rychnovsky ............... 514/185 |
| 2004/0092557 | A1 | 5/2004 | Zhang et al. |
| 2004/0110846 | A1 | 6/2004 | Leveugle |
| 2010/0047178 | A1 | 2/2010 | Sharma et al. |

FOREIGN PATENT DOCUMENTS

| | | |
|---|---|---|
| WO | WO9704836 | 2/1997 |
| WO | WO9832370 | 7/1998 |
| WO | WO 98/33470 | 8/1998 |
| WO | WO 98/52609 | 11/1998 |
| WO | WO 98/52610 | 11/1998 |
| WO | WO 99/65517 | 12/1999 |
| WO | WO 01/12217 | 2/2001 |
| WO | WO 02/060483 | 8/2002 |
| WO | WO 02/062386 | 8/2002 |
| WO | WO03089063 | 10/2003 |
| WO | WO2007016762 | 2/2007 |

OTHER PUBLICATIONS

Brancaleon et al. "Laser and non laser light sources for photodynamic therapy" Lasers in Medical Science, 2002, 17(3) 173 186.

Carpenter et al. "Cehmiluminescence activation of antiviral activity of hypericin: A molecular flashlight" Proceedings of the National Academy of Science of the United State of America, 1994, 91, 12273 12277.

Diwu et al. "Phototherapeutic potential of alternative photosensitizers to porphyrins" Pharmacology and Therapeutics, 1994, 63, 1 35.

Donnelly et al, "Topical bioadhesive patch system enhance selectivity of ptotoporphyrin IX accumulation" Photochemistry and Photobiology, May 2006, 82, 670 675.

Dougherty et al. "Photodynamic therapy" European journal of Cancer, 1992, 28(10), 1734 1742.

Henderson et al. "How does photodynamic therapy work?" Photochemistry and Photobiology, 1992, 55(1), 145 157.

Juzeniene et al. "Effectiveness of different light sources for 5 aminolevulinic acid photodynamic therapy" Lasers in Medicine, 2004, 19, 139 149.

Laptev et al. "Intracellular chemiluminescense activates targeted photodynamic destruction of leukaemic cells" The British Journal of Cancer, Jul. 4, 2006, 95, 189 196.

Lee at al. "Topical photodynamic therapy for treatment of actinic keratosis using light emitted diode (LED) device" Korean Journal of Dermatology, 2005, 43(4) 469 474.

Pass "Photodynamic therapy in oncology: Mechanisms and clinical use" Journal of the National Cancer Institute, 1993, 85(6), 443 456.

Phillip et al. "Chemiluminescence and hematoporphyrin derivative: A novel therapy for mammary adenocarcinomas in mice" Oncology, 1989, 46, 266 272.

Pieslinger et al, "Characterization of a simple and homogenous irradiation device based on light emitting diodes: A possible low cost supplement to conventional light sources for photodynamic therapy" Medical Laser Application, Nov. 2006, 21, 277 283.

Sharman et al. "Role of activated oxygen species in photodynamic therapy" Methods in Enzymology, 2000, 319, 376 400.

Stables "Photodynamic therapy in dermatology" Journal of Dermatological Treatment, 1999, 10, 213 219.

Theodossiou et al. "Firefly luciferin activated rose bengal: In vitro photodynamic therapy by intracellular chemiluminescence in transgenic NIH 3T3 cells" Cancer Research, 2003, 63, 1818 1821.

Zelickson et al. "Light patch: Preliminary report of a novel form of blue light delivery for the treatment of actinic kerostasis" Dermatology Surgery, 2005, 31(3), 375 378.

Abdel-Hady et al., "Immunological and Viral Factors Associated with the Response of Vulval Intraepithelial Neoplasia to Photodynamic Therapy," Cancer Research, 2001, vol. 61, pp. 192-196.

Bellnier, "Potentiation of photodynamic therapy in mice with recombinant human tumor necrosis factor-a," J. Photochem. & Photobiol. B: Biol.,1991, vol. 8, pp. 203-210.

Chen et al. "Structure of hypocrellin and its photooxidation product peroxyhypocrellin," Liebigs Ann, Chem., 1981, p. 1880 (English translated abstract).

Cho et al., "Effects of Photodynamic Therapy in Combination with Intravesical Drugs in a Murine Bladder Tumor Model," Journal of Urology, 1992, vol. 147, pp. 743-746.

De Vree et al., "Evidence for an Important Role of Neutrophils in the Efficacy of Photodynamic Therapy in Vivo," Cancer Research, 1996, vol. 56, pp. 2908-2911.

De Vree et al., "Role of Interleukin 1 and Granulocyte Colony-Stimulating Factor in Photofrin-based Photodynamic Therapy of Rat Rhabdomyosarcoma Tumors," Cancer Research, 1997, vol. 57, pp. 2555-2558.

Diwu et al. "Hypocrellins and Their Use in Photosensitization," Photochemistry and Photobiology, vol. 52(3), 1990, pp. 609-616.

Diwu et al., "A simple high-yielding approach to perylenequinone from the novel one-step double coupling reaction of 1 , 2-naphtoquinone." Tetrahedron, vol. 48, 1992, pp. 45-54.

Dougherty et al., "Photodynamic Therapy," J. Natl Cancer Inst. (1998) 90:889-905.

Eccles, "Monoclonal antibodies targeting cancer: 'magic bullets' or just the trigger?," Breast Cancer Res., vol. 3, 2001, pp. 86-90.

Estey et al., "Hypocrellins as photosensitizers for photodynamic therapy: a screening evaluation and pharmacokinetic study," Cancer Chemother. Pharmacol.,1996, vol. 37, pp. 343-350.

Gollnick et al., "Altered Expression of Interleukin 6 and Interleukin 10 As a Result of Photodynamic Therapy in Vivo," Cancer Research, 1997, vol. 57, pp. 3904-3909.

Hendrzak-Henion et al., "Role of the Immune System in Mediating the Antitumor Effect of Benzophenothiazine Photodynamic Therapy," Photochemistry and Photobiology, 1999, vol. 69(5), pp. 574-581.

Hirayama et al., "Photoinactivation of virus infectivity by hypocrellin A," Photochemistry and Photobiology, vol. 66 (5), Nov. 1997, pp. 697-700.

Hunt et al., "Influence of photodynamic therapy on immunological aspects of disease—an update," Exp. Opin. Invest. Drugs, 2000, vol. 9(4), pp. 807-817.

Kishi et al., "New perylenequinones from *Shiraia bambusicola*," Planta Med., vol. 57(4), Aug. 1991, pp. 376-379.

Korbelik et al., "Cancer Treatment by Photodynamic Therapy Combined with Adoptive Immunotherapy Using Genetically Altered Natural Killer Cell Line," In!. J. Cancer, 2001, vol. 93, pp. 269-274.

Korbelik et al., "Contribution of myeloid and lymphoid host cells to the curative outcome of mouse sarcoma treatment by photodynamic therapy," Cancer Letters, 1999, vol. 137, pp. 91-98.

Korbelik et al., "Enhanced Macrophage Cytotoxicity Against Tumor Cells Treated With Photodynamic Therapy," Photochemistry and Photobiology, 1994, vol. 60(5), pp. 497-502.

Korbelik et al., "Enhancement of tumour response to photodynamic therapy by adjuvant mycobacterium cell-wall treatment," J. Photochem. & Photobio. B: Biology, 1998, vol. 44, pp. 151-158.

Korbelik, M ., "Induction of Tumor Immunity by Photodynamic Therapy." J. Clin. Laser Medicine & Surgery, 1996, vol. 14 (5), pp. 329-334.

Korbelik et al., "Interaction Between Photodynamic Therapy and BCG Immunotherapy Responsible for the Reduced Recurrence of Treated Mouse Tumors," Photochem. & Photobio., 2001, vol. 73(4), pp. 403-409.

Korbelik et al., "Photodynamic Therapy-mediated Immune Response against Subcutaneous Mouse Tumors," Cancer Research, 1999, vol. 59, pp. 1941-1946.

Korbelik et al., "The Role of Host Lymphoid Populations in the Response of Mouse EMT6 Tumor to Photodynamic Therapy," Cancer Research, 1996, vol. 56, pp. 5647-5652.

Krosl et al., "Induction of immune cell infiltration into murine SCCVII tumour by Photofrin-based photodynamic therapy," Brit. J. of Cancer, 1995, vol. 71, pp. 549-555.

Krosl et al., "Potentiation of Photodynamic Therapy-elicited Antitumor Response by Localized Treatment with Granulocyte-Macrophage Colony-stimulating Factor," Cancer Research, 1996, vol. 56, pp. 3281-3286.

Miller et al., "Immunophotodynamic Therapy: Current Developments and Future Prospects", Drug Development Research, vol. 42, 1997, pp. 182-198.

Miller et al., "Preclinical Assessment of Hypocrellin Band Hypocrellin B Derivatives as Sensitizers for Photodynamic Therapy of Cancer: Progress Update," Photochem. & Photobio., 1997, vol. 65(4), pp. 714-722.

Mothilal et al., "Photosensitization with anthraquinone derivatives: optical and EPR spin trapping studies of photogeneration of reactive oxygen specie," J. Photochem. & Photobiol, A: Chemistry, vol. 162(1), Feb. 20, 2004, pp. 9-16.

Myers et al., "Modulation of Hematoporphyrin Derivative-Sensitized Phototherapy with Corynebacterium Parvum in Murine Transitional Cell Carcinoma," Urology, 1989, vol. 33(3), pp. 230-235.

Ochsner, M., "Photophysical and photobiological processes in the photodynamic therapy of tumours," J. Photochem. & Photobio. B: Biology, 1997, vol. 39, pp. 1-18.

Paul et al., "Biophysical evaluation of two red-shifted hypocrellin B derivatives as novel PDT agents," J. Photochem. & Photobiol. B: Biology, vol. 94, 2009, pp. 38-44.

Rajendran el al., "Photodynamic effects of two hydroxyanthraquinones," Biochemica et Biophysica Acta, vol. 1622(2), 2003, pp. 65-72.

Wan et al., "Hypocrellin A—A New Drug for Photochemotherapy," Kexue Tongbao (English Edition), vol. 26(11), Nov. 1981, pp. 1040-1042.

Wang et al., "Pharmacokinetics, Tissue Distribution and Photodynamic Therapy Efficacy of Liposomal-Delivered Hypocrellin A, a Potential Photosensitizer for Tumor Therapy," Photochem. & Photobiol., vol. 70(5), 1999, pp. 773-780.

Wu et al., "New potential photodynamic therapeutic anti-cancer agents: synthesis and characterization of demethoxy amino-substituted hypocrellins," Anti-Cancer Drug Design, 2000, vol. 15, pp. 287-293.

Wu et al., "Synthesis of demethoxy amino substituted hypocrellins: novel photosensitizers for photodynamic therapy," Chinese Chemical Letters, vol. 11(11), 2000, pp. 963-966.

Xu et al. "A novel method for the preparation of amino-substituted hypocrellin B," Bioorganic and Medicinal Chemistry Letters, vol. 11, 2001, pp. 2045-2047.

Xu et al., "Synthesis and characterization of three novel amphiphillic aminated hypocrellins as photodynamic therapeutic agents," Photochemistry and Photobiology, vol. 78(4), 2003, pp. 411-415.

Zhang et al., "Antisense bcl-2 retrovirus vector increases the sensitivity of a human gastric adenocarcinoma cell line to photodynamic therapy," Photochemistry and Photobiology, vol. 69(5), May 1999, pp. 582-586.

Zhang et al. "A novel photosensitizer, 2-butylamino-2-demethoxy-hypocrellin A (2-BA-2-DMHA) 1. Synthesis of 2-BA-2-DMHA and its phototoxicity to MGC803 cells," J. Photochem. & Photobiol. B, vol. 15;44(1), Jun. 1998, pp. 21-28.

Zou et al., "Damage to pBR322 DNA photosensitized by hypocrellin A in liposomes and its derivative in solution," J. Photochem. & Photobiol., vol. 33, 1996, pp. 73-78.

* cited by examiner

METHOD AND DEVICE FOR PHOTODYNAMIC THERAPY

CROSS REFERENCE TO RELATED APPLICATION

This application is a national stage application under 35 U.S.C. 371 of PCT Application No. PCT/CA2007/001290 having an international filing date of 19 Jul. 2007 which designated the United States, which PCT application claimed the benefit of U.S. Provisional Application No. 60/820,171, filed 24 Jul. 2006.

BRIEF DESCRIPTION OF THE PRIOR ART a) Field of the Invention
The invention relates to the field of photodynamic therapy.
b) Background of the Invention
Photodynamic therapy (PDT) has progressed significantly over the past decade with the advent of novel photosensitizers. However PDT requires sophisticated instrumentation to perform the light activation treatment that requires the supervision of medical practitioners. There is therefore a need for improved PDT treatment modalities which will have broadened applications in medicine and cosmetology, and which may be used safely in the absence of supervision.

SUMMARY OF THE INVENTION

There is provided a photodynamic therapy method for treating an individual in need thereof comprising administering a photosensitizer to the individual and activating the photosensitizer with a chemiluminescent light source or a light-emitting diode (LED) light source, wherein the source is in dermal contact with the individual.

In another aspect of the invention there is provided a device for photodynamic therapy comprising a permeable reservoir containing a photosensitizer formulation which may be released into the skin, and a light source; the device adapted to deliver the photosensitizer to the subject and to irradiate a part of the subject to activate the photosensitizer.

In accordance with the present invention, there is provided a photodynamic therapy method for treating a subject in need thereof comprising:
 a) administering a photosensitizer to said subject; and
 b) activating said photosensitizer with a chemiluminescent light source, and/or a light-emitting diode light source.

The chemiluminescent light source may be comprised in a device comprising a permeable reservoir for containing a photosensitizer formulation for skin application, and a light source; the device being adapted to deliver said photosensitizer to said subject and to irradiate a part of said subject to activate said photosensitizer.

The light-emitting diode light source may be a device adapted to irradiate a part of said subject to activate said photosensitizer.

The device may be a dermal patch.

The chemiluminescent light source may be from a chemical reaction between a chemiluminescent dye and a catalyst.

The chemiluminescent dye may be selected from 9,10-diphenylanthracene, 9,10-bis(phenylethynyl)anthracene, 1-chloro-9,10-bis(phenylethynyl)anthracene, rubrene, 5,12-bis(phenylethynyl)-naphthacene, rhodamine 6G, rhodamine B and said catalyst may be hydrogen peroxide.

The photosensitizer is at least one selected from the group consisting of hypocrellin B and its functional derivatives, fluoresceins, indocyanine green, rhodamine, triphenylamines, polymethines, cyanines, phthalocyanines, naphthocyanines, merocyanines, fullerenes, oxatellurazoles, verdins, rhodins, perphycenes, sapphyrins, rubyrins, metalloporphyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl)phenylproprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3β-ol, 22-(N-(7-nitrobenz-2-oxa-1,3-diazol-4-yl)amino)-23,24-bisnor-5-cholen-3β-yl cis-9-octadecenoate, 1-pyrenemethyl 3-(hydroxy-22,23-bisnor-5-cholenate, 1-pyrenemethyl 3β-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)methyl-7-hydroxycoumarin) chloride, 2-dodecylresorufin, 4-heptadecyl-7-hydroxycoumarin, 5-hexadecanoyl-aminoeosin, N-octadecyl-N'-(5-(fluoresceinyl))-thiourea, octadecyl rhodamine B chloride, 2-(3-(diphenylhexatrienyl)propanoyl)-1-hexadecanoyl-sn-glycero-3-phosphocholine, 6-N-(7-nitrobenz-2-oxa-1,3-diazol-4-yl)amino)hexanoic acid, 1-hexadecanoyl-2-(1-pyrenedecanoyl)-sn-glycero-3-phosphocholine, 1,1'-dioctadecyl-3,3,3',3'-tetramethylindocarbocyanine perchlorate, 12-(9-anthroyloxy)oleic acid, 5-butyl-4,4-difluoro-4-bora-3a,4a-diaza-s-indacene-3-nonanoic acid, N-(lissamine rhodamine B sulfonyl)-1,2-dihexadecanoyl-sn-glycero-3-phosphoethanolamine, triethylammonium salt, phenylglyoxal monohydrate, naphthalene-2,3-dicarbox-aldehyde, 8-bromomethyl-4,4-difluoro-1,3,5,7-tetramethyl-4-bora-3a,4a-diaza-s-indacene, o-phthaldialdehyde, lissamine rhodamine B sulfonyl chloride, 9-anthronitrile, 1-pyrenesulfonyl chloride, 4-(4-(dihexadecylamino)styryl)-N-methylpyridinium iodide, texaphyrins, texaphyrin-metal chelates, chlorins, chlorine-6, bonellin, mono-L-aspartylchlorine6, mesochlorin, mesotetraphenylisobacteriochlorin, mesotetraphenylbacteriochlorin, hypocrellin B, purpurins, octaethylpurpurin, zinc(II) etiopurpurin, tin(IV) etiopurpurin, tin ethyl etiopurpurin, lutetium texaphyrin, photofrin, protoporphyrin IX, tin protoporphyrin, porphyrins, benzoporphyrins, hematoporphyrin, methylpheophorbide-α-(hexyl-ether), porphycenes, ketochlorins, sulfonated tetraphenylporphines, δ-aminolevulinic acid, chlorophyll, carotenoids, flavonoids, bilins, phytochromes, phycobilins, phycoerythrin, phycocyanines, retinoic acid, retinoins and retinates.

The photosensitizer is at least one selected from the group consisting of a compound of formula (Ia) or (Ib) or stereoisomer or atropisomer thereof:

(Ib)

[Chemical structure diagram showing a polycyclic aromatic compound with OH, O, R₁, X, Y, CH₃, COR₂, OR₂, R₂O substituents]

wherein

X and Y are independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, or —$C(O)NH_2$, said $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —$CH_2$—, —$CHR_3$—, —$CH_2$—CH=CH—, —$CHR_3$—CH=CH—, or —$CH_2$—CH=$CR_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is halogen atom, hydroxy, sulphydral (—SH), an amino acid residue, carboxy, thiol, azide, nitro, $SO_3H$, —COH, —$COR_1$, —$(CH_2)_mOR_1$, —$CO_2H$, —$CO_2R_1$, —$C(O)N(R_1)_2$ —$C(O)NH(R_1)$, —$C(O)NH_2$, —$HNC(O)R_1$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and m is an integer having a value of 1 to 13;

or a pharmaceutically acceptable salt thereof.

In accordance with the present invention, there is also provided a use of a light source for activation of a photosensitizer in situ in a subject, such as to improve a skin or nail condition, or to cause hair removal.

The light source may be chosen from a chemiluminescent light source or a light-emitting diode light source.

The skin or nail condition may be chosen from: removal of a wart, acne, mole, cold sore, mild dermatitis, skin blemish of bacterial, fungal and/or viral origin, actinic keratosis, eczema, basal cell carcinoma, squamous cell carcinoma, malignant melanoma, Kaposi sarcoma, Bowen's disease, psoriasis, rosacea, vitiligo, skin ulcer, scabies, ringworm, furuncle, carbuncle, impetigo, ecthyma, folliculitis, urticaria, shingles, skin rash, allergic hypersensitivity, intractable dermatitis, hydradentis suppurativa, dermatophyte infections, candidiasis, depigmentation, exfoliation, mole, port wine stain, pigmented birthmark, age spot, liver spot, tattoo, slowing or reducing photoaging, skin rejuvenation, and spider nevi.

The hair removal may be body hair removal, or depilation.

The light source may be a chemiluminescent light source from a chemical reaction between a chemiluminescent dye and a catalyst.

The chemiluminescent dye may be selected from 9,10-diphenylanthracene, 9,10-bis(phenylethynyl)anthracene, 1-chloro-9,10-bis(phenylethynyl)anthracene, rubrene, 5,12-bis(phenylethynyl)-naphthacene, rhodamine 6G, rhodamine B and the catalyst is hydrogen peroxide.

In accordance with the present invention, there is also provided a device for photodynamic therapy comprising:

a first permeable reservoir, for containing a photosensitizer formulation for topical application on a subject for activation by light.

The device may be a dermal patch.

The device may further comprise a skin-contacting layer, located between the first permeable reservoir and the skin, which comprises a soothing element and/or a topical desensitizing agent.

The first permeable reservoir may further contain a topical desensitizing agent.

The device may further comprise a light source to activate the photosensitizer in situ.

The light source is to be located substantially over the first reservoir, to activate the photosensitizer in situ.

The light source is a chemiluminescent light source or a light-emitting diode light source.

The device may further comprise a second reservoir having an outer membrane with an inner reflective surface and containing reactants in separate compartments; wherein separation of the compartments is disrupted to cause a chemical reaction to generate chemiluminescence.

The light source may be a chemiluminescent light source from a chemical reaction between a chemiluminescent dye and a catalyst.

The chemiluminescent dye may be selected from 9,10-diphenylanthracene, 9,10-bis(phenylethynyl)anthracene, 1-chloro-9,10-bis(phenylethynyl)anthracene, rubrene, 5,12-bis(phenylethynyl)-naphthacene, rhodamine 6G, rhodamine B and the catalyst may be hydrogen peroxide.

The device may further comprise a light-emitting diode light source to activate the photosensitizer in situ.

The light-emitting diode light source is to be located substantially over the first reservoir to activate the photosensitizer in situ.

The device may further comprise an optical filter and/or a light scattering filter.

The device may further comprise a timing device and/or a cooling device.

The light-emitting diode light source may comprise a single light-emitting diode or an array of light-emitting diodes.

The light-emitting diode array may comprise light-emitting diodes emitting at the same wavelength output and/or at different wavelength output.

The light-emitting diode light source may be comprised of a flexible material adjustable to the contour of the skin.

All references referred herein are hereby incorporated by reference.

DETAILED DESCRIPTION OF THE INVENTION

There is provided a method for carrying out photodynamic therapy (PDT) which comprises administering a photosensitizer to a patient and activating the photosensitizer with a chemiluminescent light source that is preferably in dermal contact with the patient.

There is further provided a method for carrying out PDT which comprises administering a photosensitizer to a patient and activating the photosensitizer with a light-emitting diode (LED) light that is preferably in close proximity to the skin of the patient. In one embodiment the treatment is for the treatment of skin diseases or cosmetic dermatology.

The photosensitizer can be administered by various routes such as intravenous, intraarterial, intramuscular and the like but is preferably administered topically. Activation of topically applied photosensitizers for photodynamic therapy can be achieved using any of the family of chemiluminescent light sources based upon existing technology such as the Cyanalume™ technology invented by Cranor and assigned to Cyalume Technologies Inc. More recent means of generating chemiluminescence may also be used.

Activation can also be achieved with a LED light source based upon existing technology such as the high-powered LED light available from Diamond Marketing Ltd. More recent LED light sources may also be used.

Thus the invention consists of application to the surface of the skin of a photosensitizer such as a topical formulation of SL-017 or any photosensitizer for photodynamic therapy (PDT) in current use, or under development. Following the appropriate interval for biodistribution to the desired site of activity, the photosensitizer is activated with light generated by a chemiluminescent light source, such as Cyalume® Lightshape patches and/or with a high-powered LED light from Diamond Marketing Ltd. For cosmetic uses, the invention can be used as an over-the-counter (OTC) kit. The kit can be used either in a cosmetology or dermatology clinical setting, or in the client's home. For medical uses, the invention can be used in a medical clinic, or at home by the patient under a doctor's, or health care professional's, prescription or supervision.

Potential cosmetic uses include, but are not limited to: depilation, depigmentation, exfoliation, removal of warts, moles, cold sores, port wine stains, pigmented birthmarks, age spots, liver spots, tattoos, acne, mild dermatitis, skin blemishes of bacterial, fungal or viral origin. Uses include slowing or reducing photoaging, skin rejuvenation as well as improvement of rosacea, vitiligo, skin ulcers, scabies, spider nevi, ringworm, furuncles, carbuncles, impetigo & ecthyma, folliculitis, and urticaria.

This form of PDT can also be used to stimulate fibroblast proliferation in the germinal layer of skin to inhibit or reverse aging effects. New fibroblasts will generate collagen and rejuvenate skin without injection of bovine collagen and risk of immune reaction or infection. The invention may replace botox and its associated side effects.

Potential medical uses include, but are not limited to: psoriasis, actinic keratosis, hirsutism, acne, warts, moles, port wine stains, pigmented birthmarks, Kaposi's sarcoma, eczema, superficial fungal infections, bacterial infections, viral infections, shingles, skin rash, urticaria, allergic hypersensitivity, intractable dermatitis, rosacea, vitiligo, skin ulcers, scabies, spider nevi, ringworm, furuncles, carbuncles, impetigo & ecthyma, folliculitis, hydradenitis suppurativa, erythrasma, dermatophyte infections, candidiasis and the like.

Without the photosensitizer, large, self-adhesive chemiluminescent patches can be used to combat Seasonal Affective Disorder (SAD). The patches may be worn on the limbs or torso during work or sleep, alleviating the need to sit confined to a high-intensity light. Also, this might have applications without the photosensitising moiety for treatment of vitamin D deficiency in people whose solar exposure is limited, and luminescent pads in a neonatal bed may be used to treat jaundice in newborns.

In one embodiment the PDT therapy of the invention can be used for body hair removal. A thin, flexible, dermal patch containing a layered topical formulation of SL-017 and a chemiluminescent light source is applied to a client's skin where removal of hair is desired. In another embodiment of the invention, a topical formulation of SL-017 is directly applied to a client's skin where hair removal is desired. Following the appropriate interval for biodistribution of the photosensitizer SL-017 to the hair follicles, the patient activates a chemiluminescent source and/or a LED light source to activate the photosensitizer. Following exposure to light for a period of a few hours, the LED light is turned off, and/or the chemiluminescent source is depleted, and the patch is removed by the client. Permanent, or semi-permanent hair loss ensues at the treated site.

The photosensitizer can be applied as a topical gel, in solution, or in a patch resembling a Nicoderm™ patch, a bandage, or in any form which facilitates permeation of the photosensitizer to the target within the dermis, epidermis, or underlying tissues. Following distribution to the desired target (hair follicle, germinal layer of skin, sebaceous gland, mole, etc.), the photosensitizer is illuminated by a chemiluminescent patch and/or a LED light which is activated by the client, by a cosmetologist, a physician or the like; in the home or in the clinic.

The chemiluminescent patch may be applied separately upon its activation, or be integrated into a layered patch consisting of an appropriate topical formulation of photosensitizer, with an overlay of inert chemiluminescent medium, which may be activated by mixing upon rupture of a container such as a glass minivial or plastic tube which may release the catalyst (typically hydrogen peroxide) into the medium of chemiluminescent reactants.

Chemiluminescent reactions are well known in the art. Briefly, chemiluminescent reactions use energy from a chemical reaction to emit light. This chemical reaction is initiated by mixing multiple chemical compounds.

In the context of the present invention the chemical components can be maintained in separate compartments and the initiation of the chemiluminescent reaction is activated when the components are brought together (by breaking a seal between the compartments for example). Example chemiluminescent activatable devices are light sticks which are well known in the art.

The chemical reaction involves several different steps. Typically a compartment holds a hydrogen peroxide solution and another compartment holds a solution containing a phenyl oxalate ester and a fluorescent dye. When the two solutions are combined hydrogen peroxide oxidizes the phenyl oxalate ester, generating a phenol and an unstable peroxyacid ester, the unstable peroxyacid ester decomposes, generating additional phenol and a cyclic peroxy compound, the cyclic peroxy compound decomposes to carbon dioxide which releases energy to the dye. Finally, the electrons in the dye atoms are excited releasing energy in the form of light when they relax to ground state.

Various means can be used to break the seal between the compartments and initiate the reaction. For example, in light sticks a glass compartment is contained within a plastic one. When the plastic is bent the glass compartment breaks open initiating the mixing of the solutions and the chemiluminescent reaction.

The duration of the reaction and therefore of light production will depend on the nature of the reactants, their concentration and their temperature. These parameters can be adjusted to the particular need of a given treatment.

It will also be appreciated that the wavelength of the light resulting from a chemiluminescent reaction will depend on the nature of the reactants.

In one example the American Cyanamid's Cyalume light sticks are based on the reaction of bis(2,4,5-trichlorophenyl-6-carbopentoxyphenyl)oxalate (CPPO) with hydrogen peroxide in the presence of a fluorophore. The fluorophores in this reaction dictate the wavelength at which the light is emitted.

A similar reaction occurs with bis(2,4,6-trichlorophenyl) oxalate (TCPO) with hydrogen peroxide.

Thus the fluorophore can be chosen to obtain the appropriate wavelength. Table 1 provides a list of non-limiting examples:

TABLE 1

Fluorescent dyes used for emission of colored light.

| | |
|---|---|
| Blue | 9,10-diphenylanthracene |
| Green | 9,10-bis(phenylethynyl)anthracene |
| Yellow | 1-chloro-9,10-bis(phenylethynyl)anthracene Rubrene |
| Orange | 5,12-bis(phenylethynyl)-naphthacene Rhodamine 6G |
| Red | Rhodamine B |

It is possible to integrate the fluorophore in the material used for the container walls. Such an arrangement may permit the use of a fluorophore within the compartment which, once activated, may excite the fluorophore in the wall between the PDT agent and the chemiluminescent activator compartment, to fluoresce. This may be advantageous if the fluorophore of the desired wavelength is not stable in the solution used for the chemiluminescence reaction.

The latter feature is of particular significance in the design of the patch, since it boosts the photon yield and places the light source immediately adjacent to the photosensitized target. Where red chemiluminescence is required, the luminescent dye may be incorporated into the membrane separating the photosensitizer and the balance of the chemiluminescent reagents, such that strong chemiluminescence is created in the intervening membrane. The upper surface of the patch can have an inner reflective surface coating, and a window for observation of the emitted light. Various colors of the chemiluminescent moiety may be chosen to provide light penetration to the appropriate target depth: visible red for deeper penetration, green for shallower penetration, or other colors as appropriate. The color of the chemiluminescent moiety may be matched with an appropriate photosensitizer to optimize treatment for the same cosmetic or medical endpoint in subjects of differing skin tone. The shape of the invention can be designed to accommodate its intended use, or location of use. For example, a moustache-shaped device appropriate for depilation of hair on the upper lip may have a shape convening to the area treated. Custom shapes can be manufactured in various sizes and configurations for tattoo removal, wart removal, etc. Various generic shapes appropriate for differing uses are also envisaged. Large patches either in separate or tandem configuration can be manufactured to suit, for example, a large surface area of a leg or the torso, for depilation, etc. The invention is intended for single, disposable use, and designed to match the photosensitizing moiety with its intended cosmetic or medical purpose, and the chemiluminescent moiety to its optimal safe activation of the photosensitizer, either in an over-the-counter, unsupervised situation, or in a supervised situation. The elements of the photosensitizing moiety and the chemiluminescent moiety can be thin and flexible and of a size and shape suited to each intended cosmetic or medical indication. For example, a facial mask to accommodate sight, breathing and oral access may be designed to treat widespread facial blemishes. The flat geometry of the invention assures even illumination of the photosensitizer, with 180-degree or $2\pi$ geometry. The chemical composition of the chemiluminescent moiety is designed to be depleted to avoid over-activation of the photosensitizer, to confer complete safety of the device. The device, in either its separate or combined applications is self-adhesive, and is worn for a long enough interval to avoid inadvertent photosensitization by ambient light. This period can be defined by the particular photosensitizer. In the case of SL-017, a typical period of application of the patch or its separate components is two hours for biodistribution of the photosensitizer, followed by 6 hours of chemiluminescent activation. The patch may be removed at the end of the treatment, since the photosensitizer can have been diluted to inactivity by natural, pharmacokinetic processes. Times of biodistribution and chemiluminescent photoactivation can be tailored to accommodate the intended treatment and skin tone of the client. The patch may incorporate soothing elements in the layer apposed to the skin, including aloe vera, or any topical desensitizing agent. Any such desensitizing agent may be incorporated directly into the photosensitizing formulation as liquid, gel, microspheres, nanoparticles, emulsions, or any effective physical form. The upper surface of the invention may incorporate other soothing agents such as aromatherapy agents or perfumes designed to mitigate anxiety originating from the underlying cosmetic irritation. They may be activated at will by massage, or physical contact to release the desired effect from microspheres, electrospray coatings, nanospheres, emulsions or gels.

Light-emitting diodes (LED) are well known in the art. Briefly, a LED is semiconductor device that emits visible light when an electric current passes through it. The output from a LED light can be white, red, blue, and other colors. The advantages of LED light includes low power requirement, high efficiency and long life, which make it highly desirable for use in portable devices. Recently, high power LED lights have been developed that vastly expanded the use of LED, especially in the field of portable flash light.

In the context of the present invention, several design parameters may be considered for construction of a portable topical LED PDT unit. The size and the shape of the invention can be designed to accommodate its intended use, or location of use. For example, a leg-shaped device appropriate for depilation of hair on the lower and/or upper leg may have a shape convening to the area treated. Custom shapes can be manufactured in various sizes and configurations for tattoo removal, wart removal, etc. Various generic shapes appropriate for differing uses are also envisaged. The invention is intended for use on various parts of the body, in close proximity to the skin. A preferred design may require the use of flexible material to conform to skin contour in order to favor optimal exposure of the skin for irradiation of the targeted region. Straps and other devices may be used to secure the light device to the body. In some cases it could be self-adhesive. The invention can consist of a single LED, or an array of LEDs may be used in order to cover a larger area.

The LED light source of the present invention is intended to deliver a calibrated amount of light in the proper wavelength matched to the photosensitizer selected. The wavelengths of emission of the light device may thus be controlled by selecting LEDs of different color output, or by the use of a filter system to allow the desirable wavelengths of light to pass through the filter. In order to control the uniformity of the light output over the treatment surface, a scattering filter may be utilized. To potentiate the treatment, a control for light intensity and a timing device may be incorporated into the device. The invention may also include a cooling system to sooth the treated area.

The present invention will be more readily understood by referring to the following examples which are given to illustrate the invention rather than to limit its scope.

EXAMPLE 1

Light Output from LED or Chemiluminescent Light Sources

The light output and the wavelength spectrum from commercially available cool light systems including LED and chemiluminescent light sources were examined for their use as PDT light sources.

Light sources. Two high powered LED light (white and red), were obtained from Diamond Marketing Ltd. and two high intensity chemiluminescent light sticks (red and orange) were obtained from Technomoves.com.

Intensity measurements. The intensity of the light output from these devices was measured using a Melles Griot light meter at the surface of the detector. The output from a 50 W halogen light bulb is also included as a reference in the study.

Wavelength spectrum for LED light device and chemiluminescent light stick. The spectral output from the LED light device and chemiluminescent light sticks was measured using an Ocean Optics USB2000 spectrometer.

Results

First, the light intensity emitted from the four devices of interest to this study was tested and summarized in Table 2 below. The output from a 50 W halogen light bulb is included as a reference in the study. The results show that the LED light systems are able to generate a significantly higher fluence than either of the two chemiluminescent light sticks. With higher light intensity, shorter exposure time is required to deliver the light dose required for the photodynamic treatment.

TABLE 2

| Light output from Various Sources Measured at Detector Surface | |
|---|---|
| Source | Fluence at Surface |
| Halogen Light (50 W) | 228 mW |
| White LED Light (9 W) Single Bulb | 34 mW |
| Red LED Light (3 W) Single Bulb | 4.4 mW |
| Red Chemiluminescent Light Stick | <1 mW |
| Orange Chemiluminescent Light Stick | <1 mW |

Figure 1:
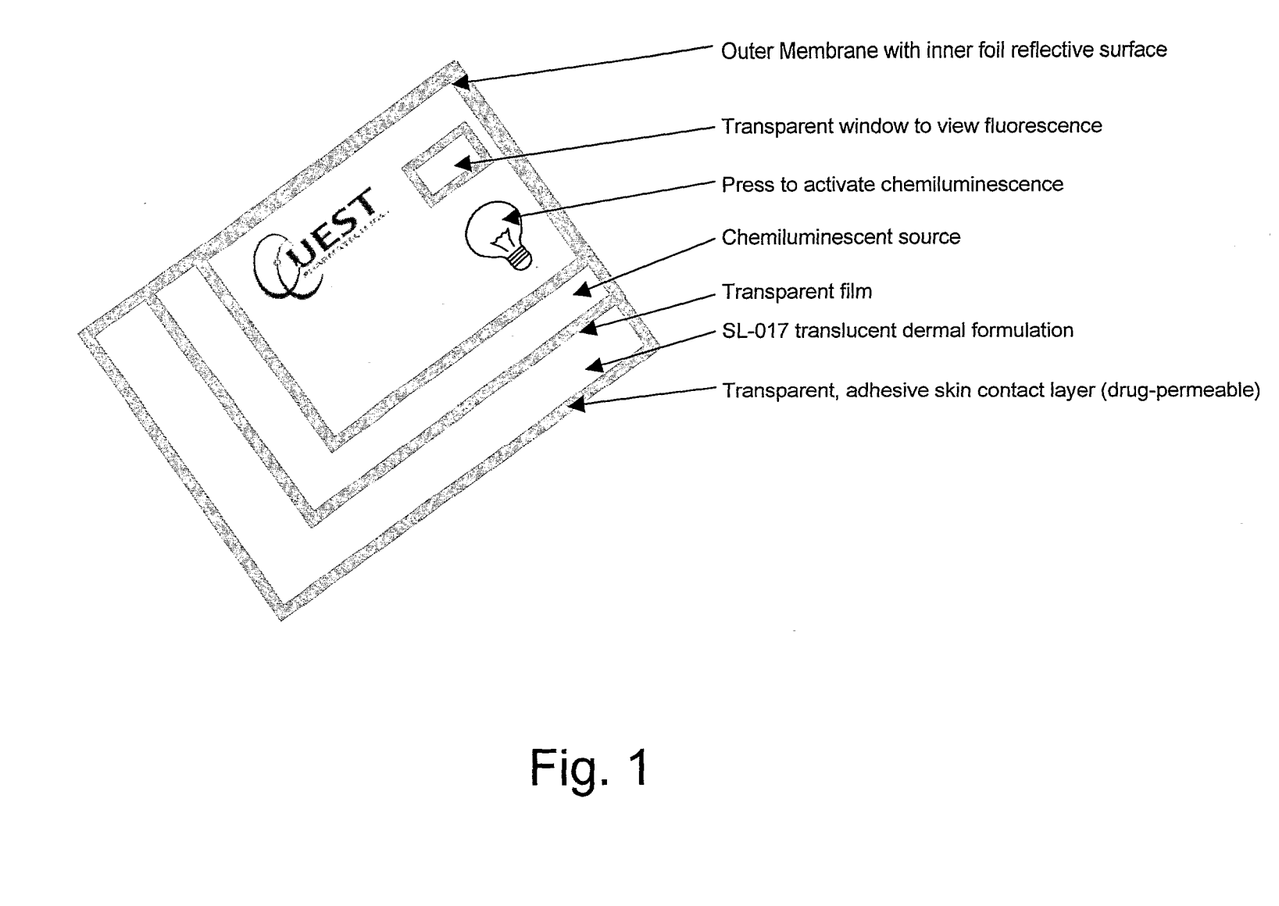
FIG. 1 illustrates a cross sectional view of a device in accordance with an embodiment of the present invention.
Figure 2:
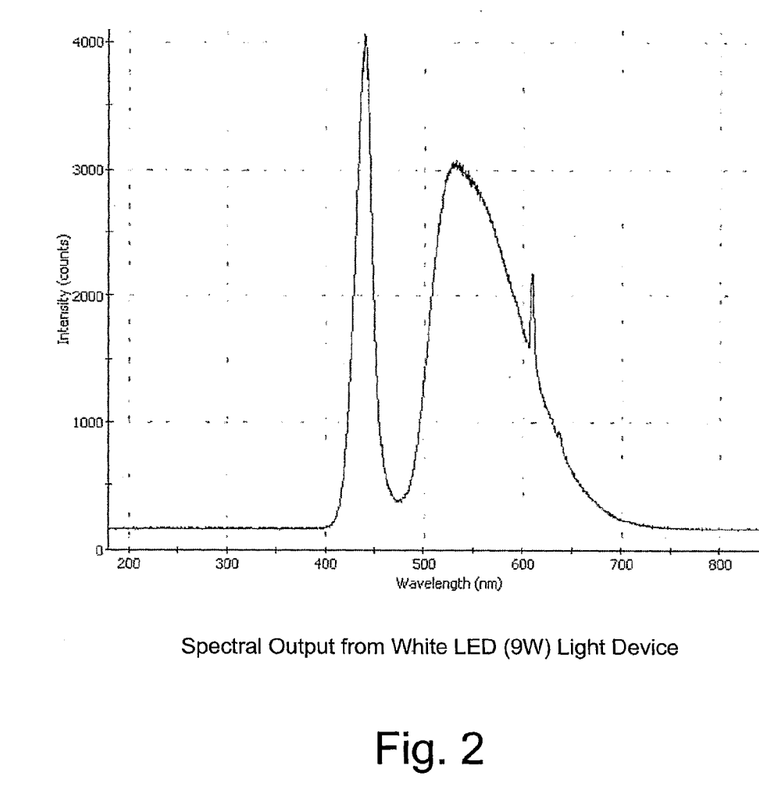
FIG. 2 illustrates the spectral output from a white LED (9W) device.
Figure 3:
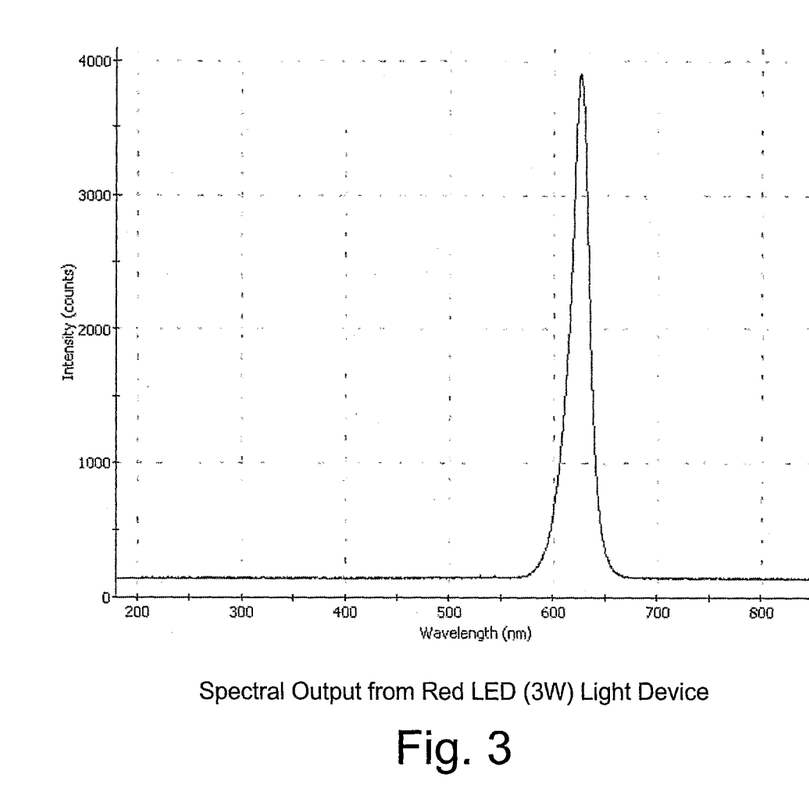
FIG. 3 illustrates the spectral output from a red LED (3W) device.
Figure 4:
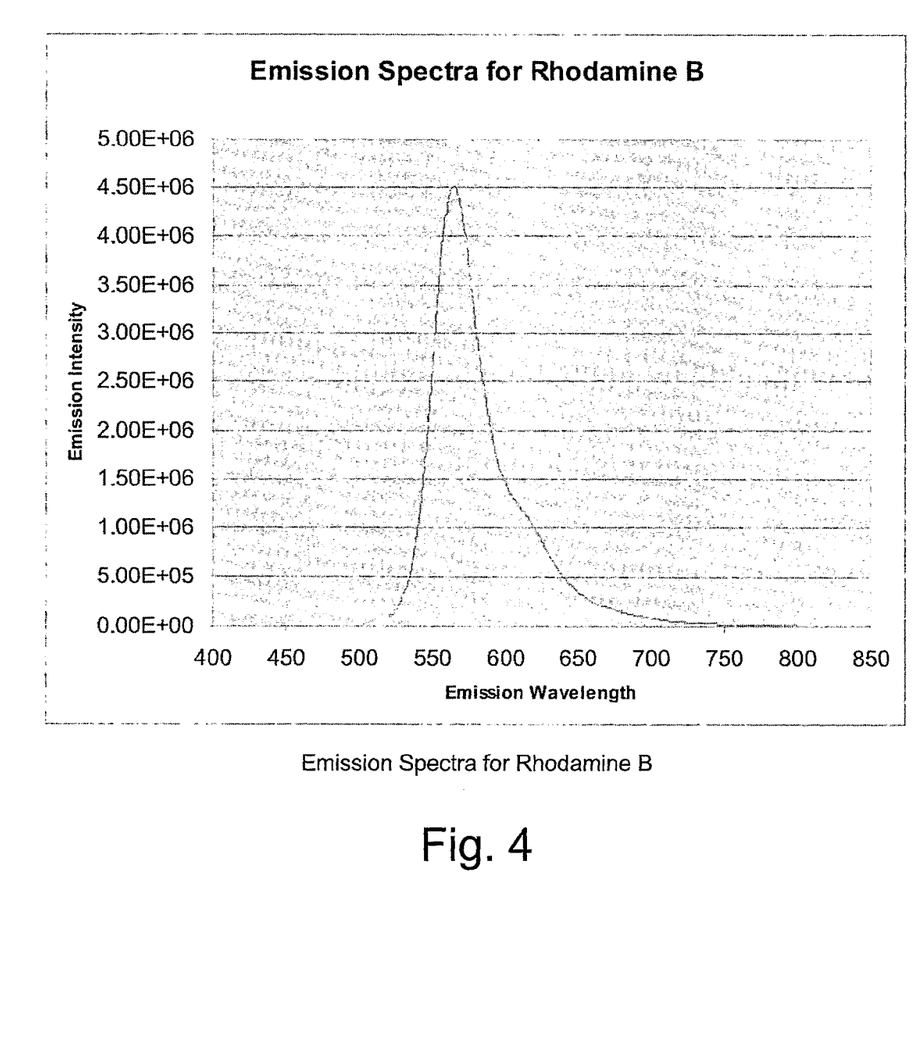
FIG. 4 illustrates the emission spectrum for rhodamine B.
Figure 5:
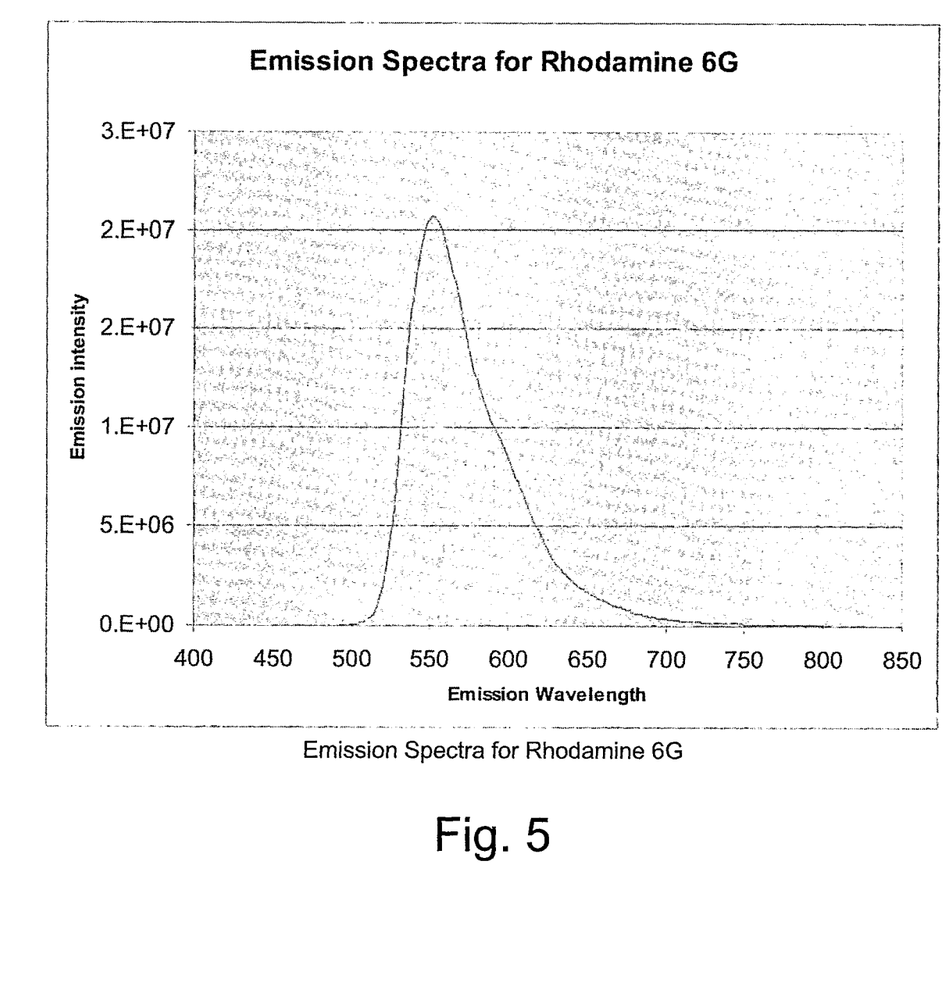
FIG. 5 illustrates the emission spectrum for rhodamine 6G.

Next, the wavelength spectrum of the devices was determined. The results obtained form the White and red LED device is summarized in FIGS. 2 and 3, while the results for the chemiluminescent red (rhodamine B) and orange (rhodamine 6G) light sticks are presented in FIGS. 4 and 5. Selection of the light devices with emission spectra that matches the absorption of the selected photosensitizer will maximize the effectiveness of the treatment and decrease the light dose required.

EXAMPLE 2

In Vitro Cell Viability Assay

The feasibility of using these alternative light sources as over the counter devices for topical PDT application is tested using an in vitro clonogenic assay to assess their ability to generate a phototoxic effect with SL-017, a known photosensitizer.

In vitro clonogenic assay. EMT-6 tumor cells are grown in culture in RPMI 1640 and plated onto Petri dishes. The photosensitizer SL-017 is added at a fixed concentration of 5 µM to the dishes and allowed to incubate for 2 hours, and then removed. The dishes are irradiated using the different two LED light sources and the orange (rhodamine 6G) chemiluminescent light source at pre-determined light doses. The EMT-6 cells are then re-plated and allowed to grow, for 5 to 7 days The number of surviving colonies in the control and treated plates are counted visually and compared.

Results

To test the usability of the light sources of PDT, EMT-6 tumor cells were grown and treated with SL-017 prior to irradiation with the light sources for a predetermined amount of time. The clonogenic assay results show that a PDT mediated toxic effect can be generated by both the white and the red LED lights (Tables 3 and 4 respectively), while the orange chemiluminescent light sticks generated such an effect less effectively (Table 5).

TABLE 3

| Results of in vitro clonogenic assay with white LED light (9 W) | | |
|---|---|---|
| Group | Number of Colonies | % Inhibition |
| Dark Control | 127.7 | N/A |
| Media Control | 112.7 | N/A |
| 0.5 J/cm$^2$ | 1.8 | 98.6% |
| 1.0 J/cm$^2$ | 0 | 100% |
| 2.0 J/cm$^2$ | 0 | 100% |

TABLE 4

Results of in vitro clonogenic assay with red LED light (3 W)

| Group | Number of Colonies | % Inhibition |
|---|---|---|
| Dark Control | 147 | N/A |
| Media Control | 152 | N/A |
| 0.1 J/cm$^2$ | 0 | 100% |
| 0.25 J/cm$^2$ | 0 | 100% |
| 0.4 J/cm$^2$ | 0 | 100% |

TABLE 5

Results of in vitro clonogenic assay with orange (rhodamine 6G) chemiluminescent light stick

| Group | Number of Colonies | % Inhibition |
|---|---|---|
| Dark Control | 125.7 | N/A |
| Media Control | 114.3 | N/A |
| 1 hour exposure | 86.3 | 31.3% |
| 2 hour exposure | 187.3 | N/A |

EXAMPLE 3

In Vivo PDT Hair Removal with White or Red LED Light Device in Mouse Skin Model

The feasibility of using these alternative light sources as over the counter devices for topical PDT application is tested using an in vivo hair removal assay to assess their ability to generate a hair removal effect on mouse skin using SL-017, a known photosensitizer.

Mouse strain. Male Balb/c mice of approximately 6 to 8 weeks of age weighing 16 to 18 grams were obtained from Charles River animal facility. The animals were allowed a minimum of 1 week to acclimatize to the facility prior to treatment.

In vivo hair removal assay. The animals were anesthetized with a 0.1 ml intra peritoneal injection of 12 mg/ml sodium pentobarbital in 0.9% Saline. An approximately 1.5×1.5 cm square area on the back of each animal was shaved and the area treated with a 2% SL-017 topical gel for 60 minutes. The excess gel was removed from the area and it was covered with a template with a 1 cm diameter opening. The open area was treated with either 15 or 30 J/cm$^2$ of light from a LED flashlight. The control group did not receive any light treatment. The mice were monitored once weekly for the re-growth of hair in the treated area. For the white LED, the treatment time required for the 15 J/cm$^2$ dose group was 5 minutes and 45 sec. while for the 30 J/cm$^2$ dose group was 11 minutes and 30 seconds. For the red LED, the treatment time required for the 15 J/cm$^2$ dose group was 45 minutes, and for the 30 J/cm$^2$ dose group was 90 minutes.

Results

The animals were monitored for re-growth of hair in the treated area. For animals irradiated with the white LED light source, no differences in the re-growth of hair were observed between the animals treated with 15 J/cm$^2$ and controls. However, for the 30 J/cm$^2$ treated group, a slight delay (<1 week) in re-growth was observed. For animals irradiated with the red LED light treatment at a dose of 15 J/cm$^2$, a delay of one week in hair re-growth in the treated area was observed. For animals treated with a higher dose of 30 J/cm$^2$, erythema is observed post treatment at the treated site. A significant delay in hair re-growth of 3 weeks is observed with this higher light dose. Hence, these alternative light sources are suitable as over the counter devices for topical PDT application.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A device for photodynamic therapy comprising:
a first permeable reservoir, for containing a photosensitizer formulation for topical application on a subject for activation by light, wherein the photosensitizer is at least one selected from the group consisting of a compound of formula (Ia) or (Ib) or stereoisomer or atropisomer thereof:

wherein
X and Y are independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_m$ $OR_1$, —$CO_2H$, —$CO_2R_1$, —$C(O)N(R_1)_2$, —$C(O)ONH$ $(R_1)$, or —$C(O)NH_2$,
said $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —$CH_2$—, —$CHR_3$—, —$CH_2$—CH=CH—, —$CHR_3$—CH=CH—, or —$CH_2$—CH=$CR_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is a halogen atom, hydroxy, sulphydral (—SH), an amino acid residue, carboxy, thiol, azide, nitro, $SO_3H$, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, —HNC(O)$R_1$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and
m is an integer having a value of 1 to 13;
and any pharmaceutically acceptable salt thereof.

2. The device as claimed in claim 1, which is a dermal patch.

3. The device as claimed in claim 1, further comprising a skin contacting layer, located between the first permeable reservoir and the skin, which comprises a soothing element and/or a topical desensitizing agent.

4. The device as claimed in claim 1, wherein said first permeable reservoir is for further containing a topical desensitizing agent.

5. The device as claimed in claim 1, further comprising a chemiluminescent light source to activate said photosensitizer in situ.

6. The device as claimed in claim 5, wherein said chemiluminescent light source is to be located substantially over said first reservoir, to activate said photosensitizer in situ.

7. The device as claimed in claim 5 further comprising a second reservoir having an outer membrane with an inner reflective surface and containing reactants in separate compartments; wherein separation of said compartments is disrupted to cause a chemical reaction to generate chemiluminescence.

8. The device of claim 5, wherein said chemiluminescent light source is from a chemiluminescent reaction between a chemiluminescent reaction catalyst and a fluorophore, wherein said fluorophore absorbs and reemits energy as light.

9. The device of claim 8, wherein said fluorophore is 9,10-diphenylanthracene, 9,10bis(phenylethynyl)anthracene, 1-chloro-9,10-bis(phenylethynyl) anthracene, rubrene, 5,12-bis(phenylethynyl)-naphthacene, rhodamine 6G or rhodamine B.

10. The device of claim 1, comprising at least one additional sensitizer selected from the group consisting of hypocrellin B and its functional derivatives, fluoresceins, indocyanine green, rhodamine, triphenylamines, polymethines, cyanines, phthalocyanines, naphthocyanines, merocyanines, fullerenes, oxatellurazoles, verdins, rhodins, perphycenes, sapphyrins, rubyrins, metalloporphyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl)phenylproprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3β-ol, 22-(N-(7-nitrobenz-2-oxa-1,3-diazol-4-yl)amino)-23,24-bisnor-5-ch-olen-3β-yl cis-9-octadecenoate, 1-pyrenemethyl 3-(hydroxy-22,23-bisnor-5-cholenate, 1-pyrenemethyl 3β-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)methyl-7-hydroxycoumarin) chloride, 2-dodecylresorufin, 4-heptadecyl-7-hydroxycoumarin, 5-hexadecanoyl-aminoeosin, N-octadecyl-N'-(5-(fluoresceinyl))-thiourea, octadecyl rhodamine B chloride, 2-(3-(diphenylhexatrienyl)propanoyl)-1-hexadecanoyl-sn-glycero-3-phosphoc-holine, 6-N-(7-nitrobenz-2-oxa-1,3-diazol-4-yl)amino)hexanoic acid, 1-hexadecanoyl-2-(1-pyrenedecanoyl)-sn-glycero-3-phosphocholine, 1,1'-dioctadecyl-3,3,3',3'-tetramethylindocarbocyanine perchlorate, 12-(9-anthroyloxy)oleic acid, 5-butyl-4,4-difluoro-4-bora-3a,4a-diaza-s-indacene-3-nonanoic acid, N-(lissamine rhodamine B sulfonyl)-1,2-dihexadecanoyl-sn-glycero-3-phosphoethanolamine, triethylammonium salt, phenylglyoxal monohydrate, naphthalene-2,3-dicarbox-aldehyde, 8-bromomethyl-4,4-difluoro-1,3,5,7-tetramethyl-4-bora-3a,4a-diaza-s-indac-ene, o-phthaldialdehyde, lissamine rhodamine B sulfonyl chloride, 9-anthronitrile, 1-pyrenesulfonyl chloride, 4-(4-dihexadecylamino)styryl)-N-methylpyridinium iodide, texaphyrins, texaphyrin-metal chelates, chlorins, chlorin e6, bonellin, mono-L-aspartylchlorine6, mesochlorin, mesotetraphenyl-isobacteriochlorin, mesotetraphenyl-bacteriochlorin, hypocrellin B, purpurins, octaethylpurpurin, zinc(II) etiopurpurin, tin(IV) etiopurpurin, tin ethyl etiopurpurin, lutetium texaphyrin, photofrin, protoporphyrin IX, tin protoporphyrin, porphyrins, benzoporphyrins, haematoporphyrin, methylpheophorbide-α-(hexyl-ether), porphycenes, ketochlorins, sulfonated tetraphenylporphines, chlorophyll, carotenoids, flavonoids, bilins, phytochromes, phycobilins, phycoerythrin, phycocyanines, retinoic acid, retinoins and retinates.

11. The device of claim 8, wherein said chemiluminescent reaction catalyst is hydrogen peroxide.

\* \* \* \* \*